United States Patent

Hong et al.

(10) Patent No.: US 8,522,653 B2
(45) Date of Patent: Sep. 3, 2013

(54) LENS SURFACE WITH COMBINED DIFFRACTIVE, TORIC, AND ASPHERIC COMPONENTS

(75) Inventors: Xin Hong, Fort Worth, TX (US); Drew Morgan, Apalachicola, FL (US)

(73) Assignee: Novartis AG, Basel (CH)

( * ) Notice: Subject to any disclaimer, the term of this patent is extended or adjusted under 35 U.S.C. 154(b) by 561 days.

(21) Appl. No.: 12/723,939

(22) Filed: Mar. 15, 2010

(65) Prior Publication Data

US 2010/0201012 A1 Aug. 12, 2010

Related U.S. Application Data

(62) Division of application No. 11/963,098, filed on Dec. 21, 2007, now abandoned.

(51) Int. Cl.
*G06F 19/00* (2011.01)
*B23B 3/00* (2006.01)

(52) U.S. Cl.
USPC ........... 82/1.11; 82/118; 82/47; 351/159.73 G

(58) Field of Classification Search
USPC ............ 82/1.11, 47, 118; 351/159.2, 159.21, 351/73, 159.73; 623/6.23, 6.3, 6.31, 6; 451/42, 451/43
See application file for complete search history.

(56) References Cited

U.S. PATENT DOCUMENTS

| 4,995,714 | A | * | 2/1991 | Cohen ..................... 351/159.41 |
| 5,120,120 | A | * | 6/1992 | Cohen ..................... 351/159.49 |
| 5,699,142 | A | * | 12/1997 | Lee et al. ................. 351/159.11 |
| 5,872,613 | A | * | 2/1999 | Blum et al. ............... 351/159.73 |
| 5,888,122 | A | * | 3/1999 | Gupta et al. .................... 451/42 |
| 7,028,595 | B2 | * | 4/2006 | Ben-Menachem et al. ...... 82/1.3 |
| 7,480,540 | B2 | * | 1/2009 | Ostendarp ..................... 700/170 |
| 7,762,667 | B2 | * | 7/2010 | Andino et al. ................ 351/212 |
| 8,092,017 | B2 | * | 1/2012 | Cano et al. ............... 351/159.74 |
| 2004/0156014 | A1 | | 8/2004 | Piers | |

FOREIGN PATENT DOCUMENTS

| EP | 0742461 A1 | 11/1996 |
| WO | 9744689 A1 | 11/1997 |
| WO | 2006060480 A1 | 6/2006 |

* cited by examiner

*Primary Examiner* — Will Fridie, Jr.
(74) *Attorney, Agent, or Firm* — Jonathan E. Prejean

(57) ABSTRACT

In one aspect, the present invention provides an intraocular lens (IOL) that includes an optic comprising an anterior surface, a posterior surface, and a plurality of diffractive zones disposed on one of those surfaces. The surface having the diffractive zones has a profile characterized by a combination of aspheric and toric components.

23 Claims, 2 Drawing Sheets

Fig. 3
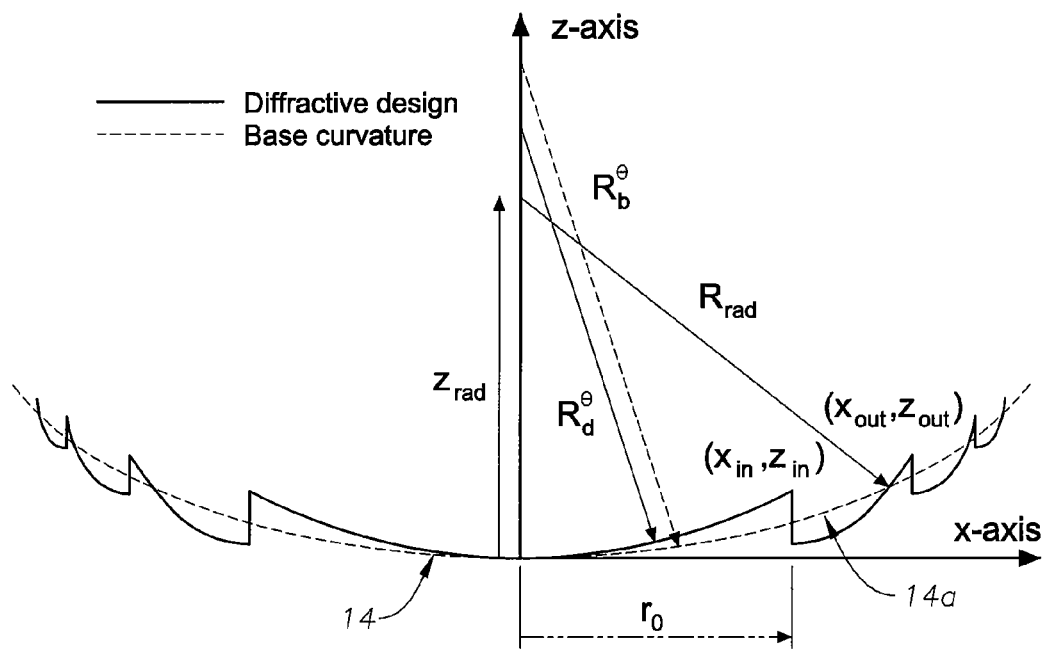
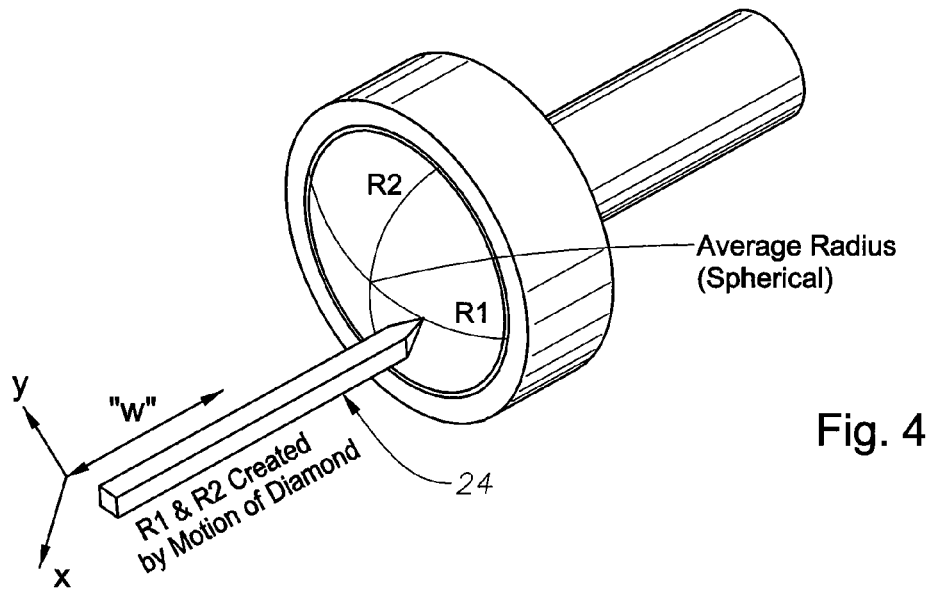
Fig. 4

LENS SURFACE WITH COMBINED DIFFRACTIVE, TORIC, AND ASPHERIC COMPONENTS

This application is a divisional application of U.S. application Ser. No. 11/963,098 filed Dec. 21, 2007 now abandoned.

BACKGROUND

The present invention is directed generally to ophthalmic lenses, and more particularly, to diffractive ophthalmic lenses that provide compensation for multiple aberrations.

Intraocular lenses (IOLs) are routinely implanted in patients' eyes during cataract surgery to replace the natural crystalline lens. In some cases, an IOL can include diffractive structures so as to have not only a far-focus power but also a near-focus power, thereby providing a degree of pseudoaccommodation. A variety of aberrations, such as spherical and astigmatic aberrations, can adversely affect the optical performance of such lenses. For example, spherical aberrations can degrade vision contrast, especially for large pupil sizes.

Diffractive IOLs that provide compensation for multiple aberrations are known. However, the fabrication of such IOLs can be time-consuming and expensive.

Accordingly, there is a need for improved ophthalmic lenses, and particularly for improved diffractive IOLs that can be more readily fabricated.

SUMMARY

The present invention relates generally to diffractive ophthalmic lenses, such as intraocular lenses (IOLs), that provide compensation for aspheric and astigmatic aberrations. In some embodiments, a single surface of the lens is shaped to include not only a plurality of diffractive structures but also a base profile that exhibits a combination of asphericity and toricity.

In one aspect, an intraocular lens (IOL) is disclosed that includes an optic comprising an anterior surface and a posterior surface, and a plurality of diffractive zones disposed on one of said surfaces (e.g., the anterior surface). The surface having the diffractive zones exhibits a base profile characterized by a combination of asphericity and toricity.

In a related aspect, the optic provides a far-focus power, e.g., in a range of about 16 to about 32 Diopters (D), as well as a near-focus power characterized, e.g., by an add power in a range of about 1 D to about 6 D.

In another aspect, a profile of the surface having the diffractive zones can be defined in accordance with the following relation:

$$\text{sag}(R_{avrg}, r, \theta) = \text{diffractive}(R_{avrg}, r) + \text{toric}(R_{avrg}, r, \theta) + \text{asph}(R_{avrg}, r)$$

wherein,
sag indicates the sag of the surface along the optical axis (e.g., z-axis) at a radial distance r from the center of the surface (intersection of the optical axis with the surface) and at a meridian angle $\theta$, where $R_{avrg}$ represents the base radius of curvature of average meridian (i.e., 45°), and diffractive($R_{avrg}$, r), toric($R_{avrg}$, r, $\theta$) and apsh($R_{avrg}$, r) represent, respectively, the diffractive, toric and aspheric components of the surface profile.

In a related aspect, the diffractive component, i.e., diffractive($R_{avrg}$, r), of the surface profile can be defined as follows:

$$\text{diffractive}(R_{avrg}, r) = z - z_{rad} - \sqrt{R_{rad}^2 - r^2}$$

wherein,
$R_{avrg}$ and r are defined as above, and $R_{rad}$ and $Z_{rad}$ denote, respectively, the radius of curvature of a diffractive zone extending through the radial distance r and an axial location (i.e., along the z-axis) of the curvature center of that zone. By way of example, $Z_{rad}$ and $R_{avrg}$ can be defined in accordance with the following relations:

$$z_{rad} = \frac{x_{in}^2 + z_{in}^2 - x_{out}^2 - z_{out}^2}{2(z_{in} - z_{out})},$$

$$R_{rad} = \sqrt{(z_{in} - z_{rad})^2 + x_{in}^2},$$

wherein, $x_{in}$ and $z_{in}$ represent, respectively, the x and z coordinates of the inner boundary (closer to the optical axis) of the diffractive zone and $x_{out}$ and $z_{out}$ denote, respectively, the x and z coordinates of the outer boundary of the diffractive zone.

In another aspect, the toric aspheric component of the surface profile can be defined in accordance with the following relation:

$$\text{toric}(R_{avrg}, r, \theta) = \frac{(c_x \cos^2\theta + c_y \sin^2\theta)r^2}{1 + \sqrt{1 - (1+k_x)c_x^2 r^2 \cos^2\theta - (1+k_y)c_y r^2 \sin^2\theta}}$$

wherein,
$R_{avrg}$, r and $\theta$ are defined as above, $c_x$ and $c_y$ represent toric curvatures along two principal meridians, and $k_x$ and $k_y$ represent toric conic constants along the two principal meridians.

In another aspect, the aspheric component of the surface profile can be defined in accordance with the following relation:

$$\text{asph}(R_{avrg}, r) = \frac{cr^2}{1 + \sqrt{1 - (1+k)c^2 r^2}}$$

wherein, $$c = \frac{1}{R_{avrg}},$$

wherein $R_{avrg}$ and r are defined as above, and k represents a spherical conic constant.

In a related aspect, in the above IOL, the magnitude of $R_{avrg}$ is in a range of about 12 mm to about 120 mm (both positive and negative signs are possible for $R_{avrg}$). In some embodiments, the magnitude of $c_x$ can be in a range of about 0.008 mm$^{-1}$ to about 0.08 mm$^{-1}$ (both positive and negative signs are possible for $c_x$), the magnitude of $c_y$ can be in a range of about 0.008 mm$^{-1}$ to about 0.08 mm$^{-1}$ (both positive and negative signs are possible for $c_y$), $k_x$ can be in a range of about −3000 (minus 3000) to about −12 (minus 12), and $k_y$ can be in a range of about −3000 (minus 3000) to about −12 (minus 12). Further, in some embodiments, the aspheric conic constant (k) can be in a range of about −3000 (minus 3000) to about −12 (minus 12).

In another aspect, the diffractive zones are formed by a plurality of diffractive structures (e.g., echelettes) that are separated from one another by a plurality of step heights. In many embodiments, each step height is constant for different meridians.

In another aspect, in the above IOL, the radius of curvature of a diffractive zone along a meridian characterized by an angle θ ($R_d^\theta$) and the radius of curvature of a base profile associated with that diffractive zone ($R_b^\theta$) are related in accordance with the following relation:

$$(n_1 - n_2)\left(\frac{1}{R_d^\theta} - \frac{1}{R_b^\theta}\right) = \text{Constant},$$

wherein $n_1$ denotes the refractive index of the material forming the optic, $n_2$ denotes the refractive index of a medium surrounding that optic, and Constant denotes a constant value. By way of example, the Constant can be in a range of about 0 (zero) Diopters to about 4 Diopters (e.g., +2 D).

In yet other aspects, the optic can be formed of a biocompatible material. Some suitable materials include, without limitation, soft acrylic polymers, hydrogel, polymethymethacrylate, polysulfone, polystyrene, cellulose, acetate butyrate, or other biocompatible materials. By way of example, in one embodiment, the optic is formed of a soft acrylic polymer (cross-linked copolymer of 2-phenylethyl acrylate and 2-phenylethyl methacrylate) commonly known as Acrysof.

In another aspect, a diffractive ophthalmic lens is disclosed that includes an optic having an anterior surface and a posterior surface. At least one of those surfaces exhibits a surface profile characterized by a combination of a diffractive, an aspheric and a toric component.

Further understanding of the invention can be obtained by reference to the following detailed description in conjunction with the associated drawings, which are described briefly below.

DETAILED DESCRIPTION

The present invention is generally directed to diffractive ophthalmic lenses that can provide compensation for both spherical and astigmatic aberrations while providing a far-focus and a near focus-power. In the embodiments that follow, the various aspects of the invention are discussed in connection with intraocular lenses (IOLs). It should, however, be appreciated that the teachings of the invention are also applicable to other ophthalmic lenses, such as contact lenses. Further, the term intraocular lens and its abbreviation "IOL" are used herein interchangeably to describe lenses that can be implanted into the interior of an eye to either replace the eye's natural crystalline lens or to otherwise augment vision regardless of whether or not the natural lens is removed.

Figure 1:
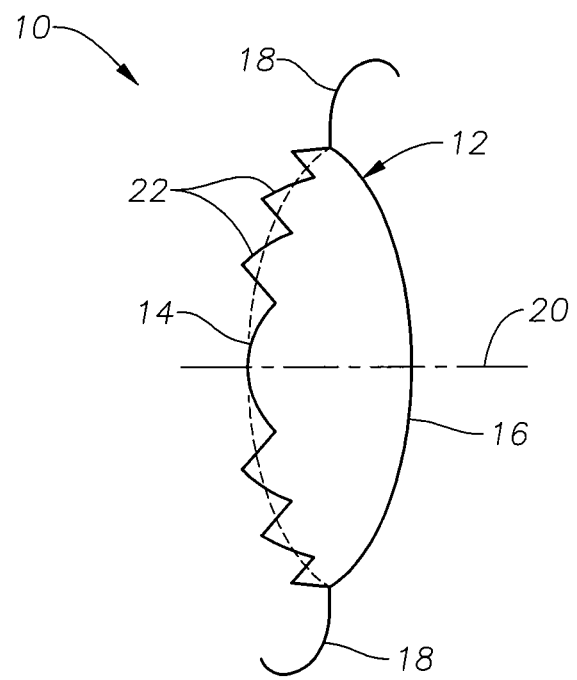
FIG. 1 is a cross-sectional view of an IOL in accordance with one embodiment of the invention.

With reference to FIG. 1, an IOL 10 according to one embodiment of the invention includes an optic 12 having an anterior optical surface 14 and a posterior optical surface 16. The IOL further includes a plurality of fixation members or haptics 18 that facilitate its placement in a patient's eye. The surfaces 14 and 16 are disposed about an optical axis 20 (which is herein also referred to as the z-axis). While the posterior surface is disposed symmetrically about the optical axis, the anterior surface exhibits asymmetry about this axis in a manner discussed below.

The optic 12 can be formed of a variety of biocompatible materials. Some examples of such materials include, without limitation, soft acrylic polymers, hydrogel, polymethymethacrylate, polysulfone, polystyrene, cellulose, acetate butyrate, or other biocompatible materials. By way of example, in one embodiment, the optic is formed of a soft acrylic material (cross-linked copolymer of 2-phenylethyl acrylate and 2-phenylethyl methacrylate) commonly known as Acrysof.

Figure 2:
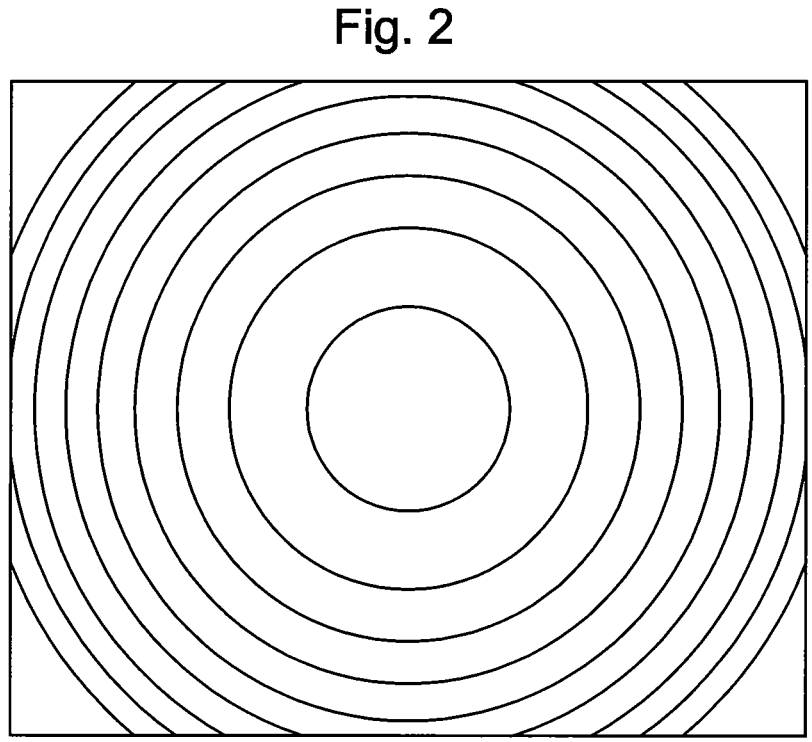
FIG. 2 is a top view of an anterior surface of the IOL of FIG. 1, and FIG. 3 schematically depicts a cross-sectional profile of the anterior surface, and FIG. 4 schematically depicts a diamond blade of an FTS system cutting a desired profile of the anterior surface into a substrate (e.g., an optical blank).

In many embodiments, the curvatures of the anterior and posterior surfaces, together with the index of refraction of the material forming the optic, are selected such that the optic provides a far focus power in a range of about −5 D to about 40 D, and preferably in a range of about 16 D to about 32 D. The anterior surface 14 further includes a plurality of diffractive zones 22 disposed on a portion thereof for providing a near-focus power. The zero$^{th}$ diffraction order of the diffractive zones 22 directs the incident light primarily to the far focus of the optic while the first diffraction order of the zones directs the incident light primarily to a near focus. The near focus can be characterized, e.g., by an add power in a range of about 1 D to about 6 D, and preferably in a range of about 3 D to about 4 D. By way of further illustration, FIG. 2 presents a top view of the anterior surface depicting that the diffractive zones are formed as annular diffractive structures separated from one another by a plurality of steps.

With reference to FIG. 1 as well as FIG. 3, the anterior surface 14 includes a base profile that deviates from a putative spherical profile, particularly at large radial distances from the optic's optical axis (z-axis), so as to exhibit a combined sphericity and toricity. In addition, as indicated above, a plurality of diffractive zones are disposed on that base profile. As such, the profile of the anterior surface 14 can be defined as formed from three components: a diffractive, an aspheric and a toric component. For example, in this embodiment, the anterior surface can be defined in accordance with the following relation:

$$\text{sag}(R_{avrg}, r, \theta) = \text{diffractive}(R_{avrg}, r) + \text{toric}(R_{avrg}, r, \theta) + \text{asph}(R_{avrg}, r) \quad \text{Eq. (1)}$$

wherein, sag indicates a sag of the surface along the z-axis (distance from the origin of the z-axis) at a radial distance r from the center of the surface (intersection of the optical axis with the surface) and at a meridian angle θ, where $R_{avrg}$ represents the base radius of curvature of average meridian (i.e., 45°), and wherein, $$\text{diffractive}(R_{avrg}, r) = z = z_{rad} - \sqrt{R_{rad}^2 - r^2} \quad \text{Eq. (2),}$$

where $R_{avrg}$ and r are defined above, and $R_{rad}$ denotes the radius of curvature of a diffractive zone extending through the radial distance r, and $Z_{rad}$ denotes an axial location (i.e., along the z-axis) of the curvature center of that zone. More specifically, $Z_{rad}$ and $R_{avrg}$ can be defined in accordance with the following relations:

$$z_{rad} = \frac{x_{in}^2 + z_{in}^2 - x_{out}^2 - z_{out}^2}{2(z_{in} - z_{out})}, \quad \text{Eq. (3)}$$

-continued $$R_{rad} = \sqrt{(z_{in} - z_{rad})^2 + x_{in}^2}, \quad \text{Eq. (4)}$$

where $x_{in}$ and $z_{in}$ represent, respectively, the x and z coordinates of the inner boundary (closer to the optical axis) of the diffractive zone and $x_{out}$ and $z_{out}$ denote, respectively, the x and z coordinates of the outer boundary of the diffractive zone. Moreover, the toric and aspheric components of the surface profile can be defined in accordance with the following relations:

$$\text{toric}(R_{avrg}, r, \theta) = \quad \text{Eq. (5)}$$
$$\frac{(c_x \cos^2\theta + c_y \sin^2\theta)r^2}{1 + \sqrt{1 - (1+k_x)c_x^2 r^2 \cos^2\theta - (1+k_y)c_y^2 r^2 \sin^2\theta}},$$

$$\text{asph}(R_{avrg}, r) = \frac{cr^2}{1 + \sqrt{1 - (1+k)c^2 r^2}}, \quad \text{Eq. (6)}$$

$$c = \frac{1}{R_{avrg}}, \quad \text{Eq. (7)}$$

where c and k represent, respectively, spherical curvature and conic constants, $c_x$ and $c_y$ represent toric curvatures along two principal meridians, and $k_x$ and $k_y$ represent toric conic constants along the two principal meridians.

When incident light rays are parallel to the anterior surface 14, the physical path differences associated with different portions of the anterior surface are equal to the sag values at different pupil locations, as defined by the above equations. A respective optical path difference for a ray passing through a portion of the lens can be calculated as the product of the physical path difference along a ray direction and the refractive index difference between the lens material and the surrounding medium. Further, in many cases in which the rays incident on the IOL are not parallel, the above equations nonetheless provide a good approximation for physical path differences corresponding to different pupil locations. For example, an IOL is typically located about 27-28 mm in front of the corneal focal plane, and a light ray at pupil margin exhibits an angle of about 6° relative to the optical axis, which introduces only a 0.6% calculation error as a result of the assumption that the ray is parallel to the optical axis.

The description of the anterior surface profile by the above Equations (1)-(7) advantageously preserves optical accuracy. Referring again to FIG. 3, taking the first diffractive zone as an example, at any given meridian ($\theta$), the radius of curvature of the first diffractive zone ($R_d^\theta$) and the respective base curvature ($R_b^\theta$) are related to the first step height (the step height between the first and second diffractive zones) according to the following relation:

$$\left(\frac{1}{2R_d^\theta} - \frac{1}{2R_b^\theta}\right)r_0^2 = \text{Step Height}, \quad \text{Eq. (8)}$$

wherein r is the radius of the first diffractive zone, as illustrated in FIG. 3.

In some embodiments, the anterior surface can be segmented across a power range, e.g., in a manner discussed above, such that the surface profiles are fixed within individual segments. The power modulation relative to the average meridian can be characterized by a constant amplitude, e.g., in terms of diopters. As the step height can be identical for different meridians and the dioptric difference is fixed (e.g., +2 D) on the average meridian, the radius of curvature of a diffractive zone and the respective base radius of curvature can be designed to create a constant dioptric difference for any angle $\theta$, as indicated in the following relation:

$$(n_1 - n_2)\left(\frac{1}{R_d^\theta} - \frac{1}{R_b^\theta}\right) = \text{Constant Diopter(e.g., + 2D)} \quad \text{Eq. (9)}$$

Referring again to FIG. 1, in this exemplary embodiment, the posterior surface 16 is spherical with a radius of curvature selected so that the lens provides a desired far-focus optical power (e.g., one in a range of about 0 to about 84 D, and preferably in a range of about 0 to about 4 D).

A variety of fabrication techniques can be employed to form the IOL 10. For example, in some embodiments, a method known as Fast Tool Servo (FTS) can be employed to impart a desired profile, such as one defined by the above Equation (1), to a surface of an optical blank formed, e.g., of a suitable biocompatible material. As shown schematically in FIG. 4, the FTS machining method uses a diamond blade 24 that can be made to move along three axes (e.g., 'X' and 'Y' axes as well as 'W' axis, which is orthogonal to the X-Y plane). More particularly, the diamond blade can be made to move—under the control of a cutting program—along the W direction in a controlled fashion, and typically at a fast rate, while concurrently conducting a two-axis motion (along X and Y axis) in a plane perpendicular to the W direction. The combined motions of the blade can result in cutting a desired profile into a surface of the optical blank. In alternative embodiments, the FTS method can be employed to form optical pins, which can, in turn, be utilized to form the IOL from a desired material.

In another fabrication technique, the generation of rotationally symmetric components (i.e., diffractive and aspheric components) can be controlled by a conventional high precision lathe (e.g., a lathe marketed by Precitech, Inc. of Keene, N.H., U.S.A.) while an FTS controls generation of the rotationally asymmetric component (i.e., the toric component). Both modules can operate independently without interfering with each other and the inputs from both modules can be combined to determine the locations of the diamond-cutting head. For example, the Precitech lathe can generate the diamond-cutting location coordinates according to diffractive ($R_{avrg}$,r)+asph($R_{avrg}$,r), which is rotationally symmetric, while the FTS can generate location coordinates toric($R_{avrg}$, r,$\theta$), which is rotationally asymmetric.

By way of example, in one embodiment, an FTS system can be programmed to pre-cut a toric geometry into an optical pin surface. Subsequently, a Precitech lathe controller can control cutting diffractive and aspheric components into the toric pin surface. Subsequently, if needed, a smaller diamond cutting tool can be employed to provide the finished optical pin surface.

Combining the diffractive, aspheric and toric components on a single surface (e.g., the anterior surface) of the IOL provides a number of advantages. For example, it facilitates the lens fabrication as the other surface (e.g., the posterior surface) can be varied for obtaining different optical powers. This can, in turn, render custom-making such IOLs for individual patients economically feasible, e.g., by drastically reducing the number of needed optical pins.

Those having ordinary skill in the art will appreciate that various changes can be made to the above embodiments without departing from the scope of the invention.

What is claimed is:

1. A method of fabricating an intraocular lens (IOL), comprising providing an optical blank comprising an anterior surface and a posterior surface;
forming a base profile on one of the surfaces, the base profile being characterized by a combination of asphericity and toricity, using a diamond cutting head positioned by a precision lathe module and a fast tool servo (FTS) module, the precision lathe module and the FTS servo module operating independently, wherein the precision lathe module generates a rotationally symmetric component of the base profile and the FTS module generates a rotationally asymmetric component of the base profile and wherein inputs from both of the modules are combined to determine a position for the diamond cutting head during the forming of the base profile; and
forming a plurality of diffractive zones on the surface having the combined base profile.

2. The method of claim 1, wherein the IOL provides a far focus and a near focus.

3. The method of claim 2, wherein said far focus provides an optical power in a range of about 16 D to about 32 D.

4. The method of claim 3, wherein said near focus provides an add power in a range of about 1 D to about 6 D.

5. The method of claim 1, wherein the base profile and the plurality of diffractive zones are formed on the anterior surface.

6. The method of claim 1, wherein a profile of said surface having the formed base profile is characterized by the following relation:

$$\mathrm{sag}(R_{avrg}, r, \theta) = \mathrm{diffractive}(R_{ave}, r) + \mathrm{toric}(R_{ave}, r, \theta) + asph(R_{ave}, r),$$

wherein,
sag represents a sag of the surface along an optical axis of the optic at a radial distance r from a center of the surface at a meridian angle $\theta$, where $R_{avrg}$ represents a base radius of curvature of average meridian, and wherein, $$\mathrm{diffractive}(R_{avrg}, r) = z_{rad} - \sqrt{R_{rad}^2 - r^2},$$

wherein,
$z_{rad}$ and $R_{rad}$ denote, respectively, a radius of curvature of a diffractive zone extending through the radial distance r and an axial location of a curvature center of that zone, and
wherein, $$\mathrm{toric}(R_{avrg}, r, \theta) = \frac{(c_x \cos^2\theta + c_y \sin^2\theta) r^2}{1 + \sqrt{1 - (1+k_x) c_x^2 r^2 \cos^2\theta - (1+k_y) c_y^2 r^2 \sin^2\theta}},$$

wherein,
$c_x$ and $c_y$ represent toric curvatures along two principal meridians of the surface and $k_x$ and $k_y$ represent toric conic constants along the two principal meridians, and
wherein, $$asph(R_{avrg}, r) = \frac{cr^2}{1 + \sqrt{1 - (1+k) c^2 r^2}},$$

and
wherein $$c = \frac{1}{R_{avrg}},$$

and
wherein k represents a spherical conic constant.

7. The method of claim 6, wherein $z_{rad}$ is defined in a Cartesian coordinate (x,y,z), where z is along the optical axis, in accordance with the following relation:

$$z_{rad} = \frac{x_{in}^2 + z_{in}^2 - x_{out}^2 - z_{out}^2}{2(z_{in} - z_{out})},$$

wherein $x_{in}$ and $z_{in}$ represent, respectively, x and z coordinates of an inner boundary of the diffractive zone and $x_{out}$ and $z_{out}$ represent, respectively, x and z coordinates of an outer boundary of the diffractive zone.

8. The method of claim 7, wherein $R_{rad}$ is defined in the Cartesian coordinates in accordance with the following relation:

$$R_{rad} = \sqrt{(z_{in} - z_{rad})^2 + x_{in}^2}.$$

9. The method of claim 8, wherein a magnitude of $R_{avrg}$ is in a range of about 12 mm to about 120 mm.

10. The method of claim 9, wherein a magnitude of $c_x$ is in a range of about 0.008 mm$^{-1}$ to about 0.08 mm$^{-1}$ and a magnitude of $c_y$ is in a range of about 0.008 mm$^{-1}$ about 0.08 mm$^{-1}$.

11. The method of claim 10, wherein kx is in a range of about −3000 to about −12 and $k_y$ is in a range of about −3000 to about −12.

12. The method of claim 11, wherein k is in range of about −3000 to about −12.

13. The method of claim 1, wherein said plurality of diffractive zones comprise a plurality of diffractive structures separated from one another by a plurality of step heights.

14. The method of claim 13, wherein a radius of curvature of a diffractive zone along a meridian characterized by an angle $\theta$ ($R_d^\theta$) and a radius of curvature of a base profile associated with that diffractive zone)($R_b^\theta$) are related in accordance with the following relation:

$$(n_1 - n_2)\left(\frac{1}{R_d^\theta} - \frac{1}{R_b^\theta}\right) = \mathrm{Constant}.$$

15. The method of claim 14, wherein said Constant is in a range of about 0 D to about 4 D.

16. The method of claim 1, wherein forming the plurality of diffractive zones comprises forming the plurality of diffractive zones on the anterior surface.

17. The method of claim 16, wherein said posterior surface exhibits a spherical profile.

18. A method of fabricating a diffractive ophthalmic lens, comprising
providing an optic having an anterior surface and a posterior surface, forming a profile characterized by a combination of diffractive, aspheric and toric components on at least one of the surfaces using a diamond cutting head positioned by a precision lathe module and a fast tool servo (FTS) module, the precision lathe module and the FTS servo module operating independently, wherein the precision lathe module generates a rotationally symmetric component of the base profile and the FTS module generates a rotationally asymmetric component of the base profile and wherein inputs from both of the modules are combined to determine a position for the diamond cutting head during the forming of the base profile.

19. The method of claim 18, wherein said lens provides a far-focus optical power in a range of about 16 D to about 32 D.

20. The method of claim 19, wherein said lens provides a near-focus power characterized by an add power in a range of about 1 D to about 6 D.

21. The method of claim 1, wherein the forming the base profile and the forming the plurality of diffractive zones steps comprises forming the base profile and forming the plurality of diffractive zones using a Fast Tool Servo (FTS) machining method.

22. The method of claim 21, comprising using the FTS machining method to form the plurality of diffractive zones and the base profile on an optical pin from which the IOL can be fabricated.

23. The method of claim 1, wherein the base profile is formed using a FTS machining method and a precision lathe and wherein the plurality of diffractive zones are formed using the precision lathe.

\* \* \* \* \*